United States Patent [19]
Ollar

[11] Patent Number: 5,981,210
[45] Date of Patent: Nov. 9, 1999

[54] METHOD FOR DETERMINING A PRESENCE OR ABSENCE OF A NONPARAFFINOPHILIC HYDROPHOBIC MICROORGANISM IN A BODY SPECIMEN BY USING A DNA EXTRACTION PROCEDURE AND A NOVEL DNA EXTRACTION PROCEDURE

[75] Inventor: Robert A. Ollar, Milford, Pa.

[73] Assignee: Infectech, Inc., Sharon, Pa.

[21] Appl. No.: 09/122,499

[22] Filed: Jul. 24, 1998

Related U.S. Application Data

[63] Continuation-in-part of application No. 08/969,587, Nov. 13, 1997.

[51] Int. Cl.$^6$ .............................. C12Q 1/04; C12Q 1/02; C12Q 1/00
[52] U.S. Cl. .................................. 435/34; 435/29; 435/4; 435/23; 435/183; 435/863; 435/872; 435/874; 435/875; 435/876; 435/877; 435/963; 435/970; 536/23.1
[58] Field of Search .................................. 435/34, 29, 4, 435/23, 183, 863, 872, 874, 875, 876, 877, 963, 970; 536/23.1

[56] References Cited

U.S. PATENT DOCUMENTS

| | | | |
|---|---|---|---|
| 5,153,119 | 10/1992 | Ollar | 435/34 |
| 5,472,877 | 12/1995 | Ollar | 435/288.1 |
| 5,569,592 | 10/1996 | Ollar | 435/286.2 |
| 5,639,675 | 6/1997 | Felder et al. | 435/29 |
| 5,641,645 | 6/1997 | Felder et al. | 435/32 |
| 5,654,194 | 8/1997 | Felder et al. | 435/287.9 |
| 5,663,056 | 9/1997 | Ollar et al. | 435/287.9 |
| 5,668,010 | 9/1997 | Felder et al. | 435/287.9 |
| 5,677,169 | 10/1997 | Ollar et al. | 435/287.9 |
| 5,846,760 | 12/1998 | Ollar | 435/34 |

*Primary Examiner*—Louise N. Leary
*Attorney, Agent, or Firm*—David V. Radack; Eckert Seamans Cherin & Mellott, LLC

[57] ABSTRACT

The method of the invention involves providing a first receptacle and a second receptacle. The first receptacle contains a sterile aqueous broth and the second receptacle contains an aqueous broth including a carbon source. The method then includes placing into the first receptacle a first support surface having a paraffin wax coating thereon and placing into the second receptacle a second support surface having a hydrophobic material coating thereon. A body specimen, such as sputum, is then introduced into each of the first and second receptacles. The presence of a nonparaffinophilic hydrophobic microorganism in the body specimen is determined by observing (i) a lack of microorganism growth on the paraffin coated material of the first support surface and (ii) a presence of microorganism growth on the hydrophobic material coating of the second support surface. The presence of the nonparaffinophilic hydrophobic microorganism can be further confirmed by performing a DNA extraction. An associated DNA extraction procedure is also provided.

17 Claims, 2 Drawing Sheets

METHOD FOR DETERMINING A PRESENCE OR ABSENCE OF A NONPARAFFINOPHILIC HYDROPHOBIC MICROORGANISM IN A BODY SPECIMEN BY USING A DNA EXTRACTION PROCEDURE AND A NOVEL DNA EXTRACTION PROCEDURE

CROSS-REFERENCE TO RELATED APPLICATION

This application is a continuation-in-part of United States Pat. application Ser. No. 08/969,587, filed Nov. 13, 1997.

BACKGROUND OF THE INVENTION

This invention relates to a method for determining a presence or absence of a nonparaff inophilichydrophobic microorganism in a body specimen by using a DNA extraction procedure and a novel DNA extraction procedure.

Several of my United States Patents disclose a method of identifying paraffinophilic and nonparaffinophilic microorganisms in a body specimen. Focussing particularly on detection of paraffinophilic microorganisms, a paraffin slide is placed into a receptacle containing a sterile aqueous broth. After this, a body specimen, such as fecal matter, is introduced into the receptacle. As the broth contains no carbon source for food for the microorganism, if the microorganism is a paraffinophilic microorganism, it will be baited by and attach to the paraffin coating on the slide in order to utilize the paraffin wax as a food/carbon source. By observing the microorganism growth on the slide, and by (if desired) performing a sequence of assays, the paraffinophilic microorganisms can be identified.

This method, however, does not eliminate the potential presence of a nonparaffinophilic hydrophobic microorganism, such as M. tuberculosis. Thus, what is needed is a simple, inexpensive and easy to use method that will allow the determination of the presence or absence of a nonparaffinophilic hydrophobic microorganism.

SUMMARY OF THE INVENTION

The method of the invention has met or exceeded the above-mentioned needs as well as others. The method of the invention involves providing a first receptacle and a second receptacle. The first receptacle contains a sterile aqueous broth and the second receptacle contains an aqueous broth including a carbon source. The method then includes placing into the first receptacle a first support surface having a paraffin wax coating thereon and placing into the second receptacle a second support surface having a hydrophobic material coating thereon. A body specimen, such as sputum, is then introduced into each of the first and second receptacles. The presence of a nonparaff inophilic hydrophobic microorganism in the body specimen is determined by observing (i) a lack of microorganism growth on the paraffin coated material of the first support surface and (ii) a presence of microorganism growth on the hydrophobic material coating of the second support surface. The presence of the nonparaffinophilic hydrophobic microorganism can be further confirmed by performing a DNA extraction.

A novel method of DNA extraction is also provided, whereby a pure DNA fraction can be separated from the microorganism which is found growing on the hydrophobic material coating thereon.

BRIEF DESCRIPTION OF THE DRAWINGS

A full understanding of the invention can be gained from the following detailed description of the invention when read in conjunction with the accompanying drawings in which.

DETAILED DESCRIPTION

As used herein, the term "paraffinophilic microorganism" means a microorganism that can employ paraffin as a source of carbon in a basal salt media, devoid of other forms of carbon. The organism may be bacterial or fungal in nature. The term shall expressly include, but not be limited to, the following microorganisms: Micrococcus Paraffinae; Corynebacterium Simplex; Ahnl; Mycococcus (Rhodococcus) Cinnabareus; Ahnl. Mycococcus (Rhodoc) Rhodochrous; Mycobact. Perrugosum Var. Athanicum; Mycobact. Rubrum Var. Propanicum; Mycobacterium Hyalinum; Mycobacterium Lacticola; Mycobacterium Album, M. Luteum; Mycobacterium Microti; Mycobacterium Rubrum, Mycobacterium Phlei.; Mycobacterium Phlei, M. Smegmatis; Mycobacterium Testudo; Mycobacterium-Avium-Intracellulare; Nocardia Spp.; Actinomyces; Candida Lipolytica; Candida Tropicalis, Torulopsis Colliculosa; Monila Sp., Hansenula Sp., Torula rossa; Penicillium Sp.; IHNL. Aspergillus Flavus; Aspergillus sp., Penicillium Sp.; Citromyces Sp., Scopulariopsis Sp.; Pseudomonas Fluorescens Liguefaciens; Ahnl, Pem. Fluorescens Denitrificans; Pseudomonas Aeruginosa; Streptomyces Spp.; and Mycobacterium Marinum.

As used herein, the term "nonparaffinophilic microorganism" means any microorganism sustained by a carbon source other than paraffin.

As used herein, the term "nonparaffinophilic hydrophobic microorganism" means a nonparaffinophilic microorganism that, when inoculated into an aqueous broth containing a dissolved carbon source, will prefer to grow upon a hydrophobic surface introduced into the broth as opposed to growing within the aqueous broth itself. Examples of such nonparaffinophilic hydrophobic microorganisms include, but are not limited to, the following: M. tuberculosis complex (M. tuberculosis, M. bovis, M. africanum, M. microti); M. paratuberculosis; M. leprae; pseudomonads; and nocardial species.

As used herein, the term "patient" refers to a member of the animal kingdom, including human beings.

Figure 1:
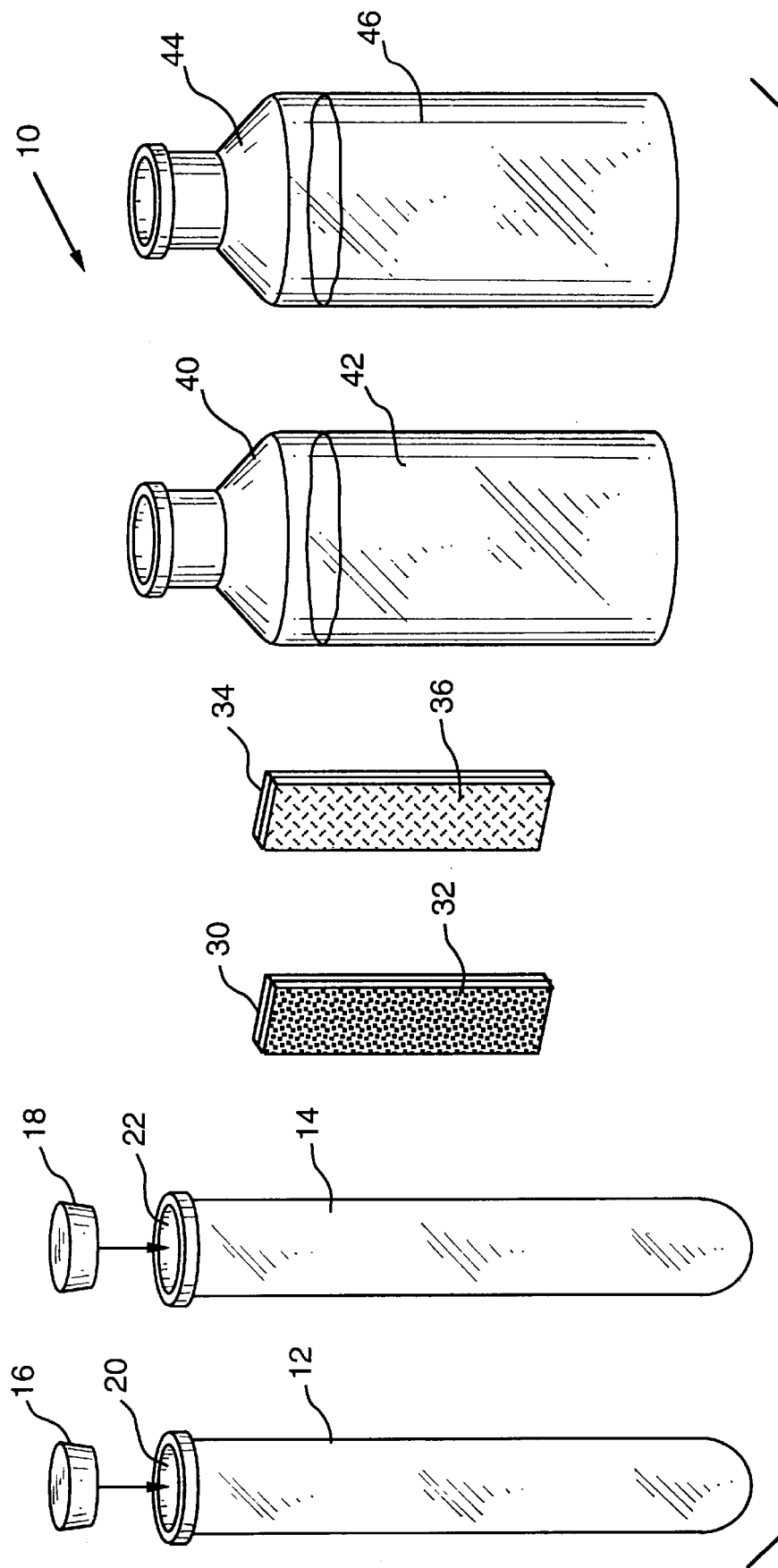
FIG. 1 is a perspective view of the various components of the kit of the invention.

Referring now to FIG. 1, the kit 10, in its disassembled form, is shown. The kit 10 consists of a first receptacle, such as a first glass test tube 12, and a second receptacle, such as a second glass test tube 14, each having respective stoppers 16, 18 (either plastic friction fit or plastic screw cap type) enclosing the respective openings 20, 22 of the test tubes 12 and 14. The kit 10 further consists of a first support surface, such as a first glass slide 30, having thereon a paraffin wax coating 32, and a second support surface, such as a second glass slide 34, having thereon a hydrophobic material coating 36 (discussed in more detail below). The kit 10 optionally can also include a first container 40 containing a sterile aqueous broth, such as Czapek broth 42, and a second container 44 containing an aqueous broth including a carbon source, the carbon being dissolved in the broth. One type of aqueous broth including a dissolved carbon source is Middlebrook 7H9 broth 46. The kit 10 can be packaged in an attractive container, such as a box (not shown), to make it suitable for sales to medical facilities, such as hospitals, laboratories or doctor's offices.

Figure 2:
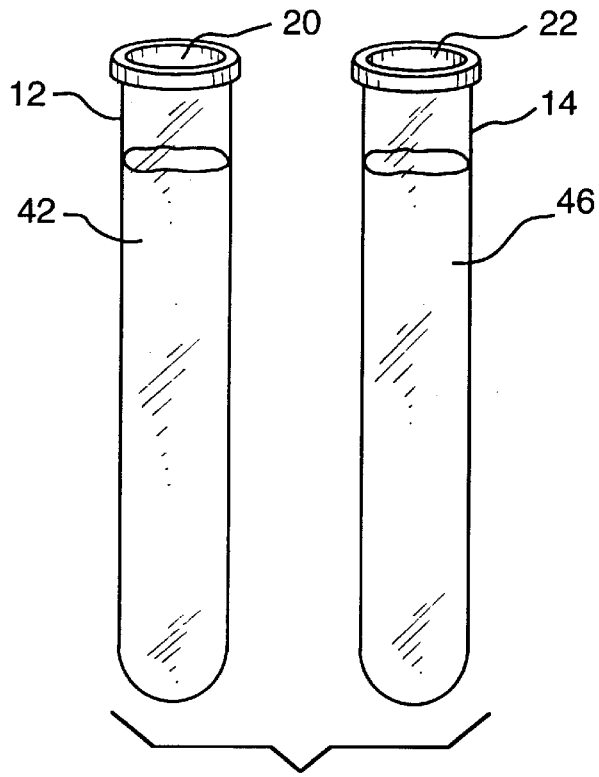
FIG. 2 is a perspective view of the two receptacles containing their respective aqueous broths.
Figure 3:
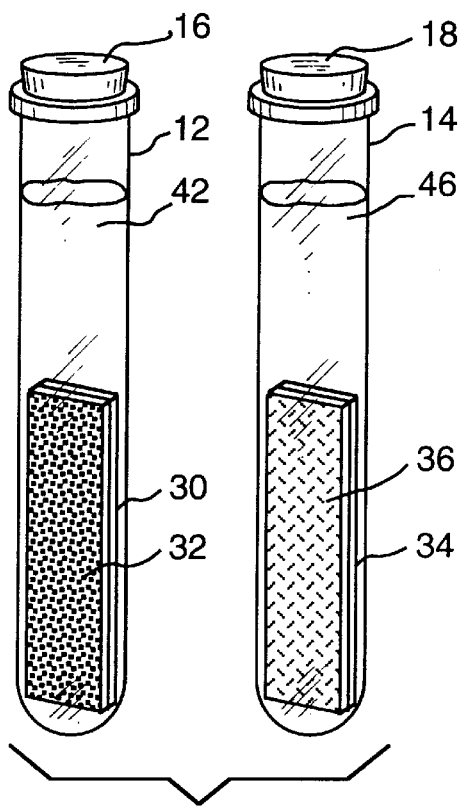
FIG. 3 is a perspective view similar to FIG. 2, only showing the respective slides and body specimens contained therein.
Figure 4:
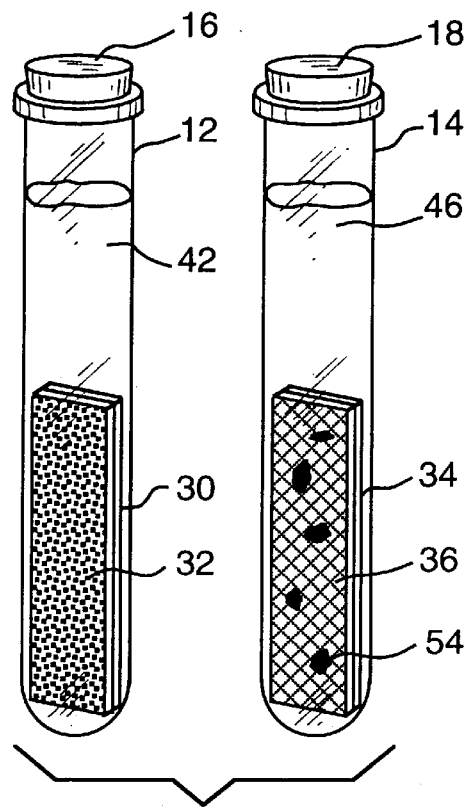
FIG. 4 is a perspective view similar to FIG. 3, only showing the lack of growth on the slide in the first receptacle and the presence of growth on the slide in the second receptacle.

With reference to FIGS. 2–4, the method of the invention will now be discussed. A body specimen is first taken from a patient. This body specimen can be sputum, fecal matter, cerebrospinal fluid, urine, gastric fluid, lymphatic material and purulent body fluids. The first test tube 12 and the second test tube 14 are taken from the kit 10 and are preferably placed side-by-side with the Czapek broth 42 being poured from the first container 40 into the first test tube 12 and the Middlebrook 7H9 broth 46 being poured from the second container 44 into the second test tube 14. After this, the first glass slide 30 having thereon the paraffin wax coating 32 and a portion of a body specimen are introduced into the Czapek broth 42 in the first test tube 12. The stopper 16 is then friction fit into the opening 20 of the first test tube. Similarly, the second glass slide 34 having thereon the hydrophobic material coating 36 and another portion of the body specimen are then introduced into the Middlebrook 7H9 broth 46 in the second test tube 14. The stopper 18 is then friction fit into the opening 22 of the second test tube 14.

If after several days (anywhere from 5–20 days), as shown in FIG. 4, there is (i) a lack of microorganism growth on the slide 30 coated with paraffin wax 32 and (ii) there is a presence of microorganism growth 54 on the second slide 34 coated with a hydrophobic material 36, it can be determined with a high rate of confidence that the body specimen contains a nonparaffinophilic hydrophobic microorganism, such as *M. tuberculosis*. This result can be further confirmed by doing an acid fastness assay (as is conventionally known and as is described in my U.S. Pat. No. 5,153,119, the disclosure of which is incorporated by reference herein).

The hydrophobic materials that can be used are paraffin wax or other waxes; plastics such as polypropylene, polyethylene, polystyrene, and tetrafluoroethylene; or silicones.

The invention utilizes the inventor's unexpected finding that *M. tuberculosis* and *M. paratuberculosis* and other microorganisms were able to grow on paraffin or other hydrophobic materials in a nutrient rich broth media, such as Middlebrook 7H9 broth. The waxy cell walls of these microorganisms, it is thought, favors attachment to a hydrophobic surface, such as paraffin wax, and thus the microorganism can imbibe the nutrients in the broth while being attached to the paraffin wax. In this way, paraffin baiting, as is described in my earlier U.S. Patents, can be combined with this so-called "hydrophobic baiting" to determine the presence or absence of these nonparaffinophilic hydrophobic microorganisms in a body specimen.

EXAMPLE

A patient comes into a doctor's office complaining of coughing, chronic fatigue, night sweats and loss of weight. The doctor suspects the patient has tuberculosis. The doctor obtains a sputum sample and introduces a portion of the sample into a first receptacle 12 containing the Czapek broth 42 only and a first slide 30 having a paraffin wax coating 32 and another portion of the sample into a second receptacle 14 containing the Middlebrook 7H9 broth 46 and a second slide 34 having a hydrophobic material coating, such as paraffin wax, 36. After several days, there is a lack of growth on the slide 30 having a paraffin wax coating 32 and there is positive growth on the slide 34 having a hydrophobic material coating 36. The doctor is fairly confident that the patient has *M. tuberculosis* and does an acid fastness assay test to confirm this conclusion.

In addition to confirming the identification of the microorganism by performing an acid fastness assay, a DNA extraction procedure can be performed. Broadly speaking, DNA extraction involves separating the pure DNA fractions from the microorganism. It has been found, quite surprisingly and unexpectedly, that the hydrophobic material 36 on which the microorganism growth 34 is attached facilitates the separation of the pure DNA fraction, as will be further explained in the detailed, novel, DNA extraction procedure discussed below.

The slide 34 containing the microorganism growth 54 on the hydrophobic material 36 of the slide 34 is first passed through three washings of sterile Czapek liquid broth. The microorganism growth 54, along with a portion of the hydrophobic material 36 on which the growth 54 is present, is scrapped off of the slide 34 into a sterile centrifuge tube with a flame sterilized spatula. It will be appreciated that the separate microorganisms, and more particularly, the cellular walls of the separate microorganisms, are attached to the portion of the hydrophobic material that has been scrapped off of the slide 34. After this, 5 ml of sterile Czapek broth is added to the sterile centrifuge tube, the tube then being vortexed, placed into a refrigerated centrifuge chamber (4° C.) and spun for 15 minutes at 1000 rpm. After spinning, the microorganism growth and the hydrophobic material are formed into a pellet, and the supernate is removed and discarded.

The pellet is then resuspended in 3 ml of Buffer #1 (10 mM Tris-HCl, 100 mM NaCl, 5 mM EDTA, pH 7.0) in a tube and vortexed. In order to crack open the cellular walls and free the crude nucleic acid fraction, which contains the pure DNA fraction, proteins and other cell material, 15 mg lysozyme is added to the tube and the tube is incubated for 20 minutes at 37° C. The lysozyme will enzymatically break open the cellular wall and the crude nucleic acid fraction will be separated therefrom. The hydrophobic material 36 acts as a cellular "garbage collector" on which is firmly adhered the unwanted cellular content, while the desired crude nucleic acid fraction escapes into solution.

After this, an aliquot of 2 ml of Buffer #2 (10 mM Tris-HCl, 250 mM NaCl, 1.2% Triton X-100, 100 mg/ml RNASE A, 12 mM EDTA, 0.5 M Guanidine-HCl, pH 8.0) is added to the previous step and placed on ice for 20 minutes. An aliquot of 35 mg of Proteinase K is added to a final concentration of 7 mg/ml. This is then incubated at 50° C. for 2 hours. The Proteinase K will destroy the proteins in the crude nucleic acid fraction.

The centrifuge tube from the preceding step is then centrifuged at 15,000 rpm at 4° C. for 15 minutes. The supernate is carefully removed and transferred to a clean sterile centrifuge tube. The centrifuge tube is then again centrifuged at 15,000 rpm to 15 minutes. The supernate is carefully removed and transferred to a clean sterile centrifuge tube. The supernate is then again centrifuged at 15,000 rpm for 15 minutes. The supernate is then again carefully removed to a new sterile centrifuge tube. The supernate in this tube will now be referred to as the "lysate" which contains the pure DNA fraction as well as other undesired cell content. An anionic column chromatograph procedure, as will be explained below, can then be used to obtain the desired DNA fraction.

A 5 ml syringe barrel filled with a 1 ml slurry of DEAE-Sephadex A25 Anionic Chromaographic Gel Matrix (Pharmacia LKB Biotechnology, Inc., Piscataway, N.J., U.S.A.) or a Qiagen "Tip-20" chromatographic column available from Qiagen, Inc. (Qiagen, Inc., Chatsworth, Calif., U.S.A.) is equilibrated with 1 ml of Buffer #3 (750 mM NaCl, 50 mM MOPS, 15% Ethanol, 0.15% Triton-X-100, pH 7.0). The lysate is now applied to the Anionic Exchange Column Matrix (AECM). The AECM column is then washed with 4 ml of Buffer #4 (1000 mM NaCl, 50 mM MOPS, 15% Ethanol, pH 7.0). The AECM column is eluted with 1 ml of Buffer #5 (1250 mM NaCl, 50 mM Tris-HCl, 15% Ethanol, pH 8.5). After all the Buffer #5 has run through the AECM column, a 20 ml syringe is employed to remove the remaining buffer. The eluate obtained in this step is dispensed into aliquots of 500 μl in microcentrifuge tubes. 500 μl of isopropyl alcohol is then added to each of the microcentrifuge tubes and the tubes are spun at 14,000 rpm for 30 minutes at 4° C. Once the supernate is removed and discarded, 1000 μl of 70% (v/v) ethanol per tube is added and the tubes are spun at 14,000 rpm for 10 minutes at 4° C. The supernate is then removed and discarded. The pellet is then resuspended in 100 μl of sterile TE Buffer (0.1 M Tris-HCl (pH 8.0), 1.0 mM EDTA) or dd $H_2O$ (double distilled deionized water), transferred to a sterile microcentrifuge tube and stored at 20° C. This provides the user with DNA that can be utilized with subsequent other applications, such as DNA amplifications and the like.

It will be appreciated that a method and kit are provided to determine the presence or absence of a nonparaffinophilic hydrophobic microorganism in a body specimen are provided. The method is simple and efficient and the kit itself is fairly inexpensive. It will be further appreciated that a novel DNA extraction procedure is also provided in order to further intensify the microorganism and to provide the user with pure DNA in order to perform DNA manipulation processes.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of determining a presence or absence of a nonparaffinophilic hydrophobic microorganism in a body specimen comprising:

providing a first receptacle and a second receptacle, said first receptacle containing a sterile aqueous broth and said second receptacle containing an aqueous broth including a carbon source;

placing into said first receptacle a first support surface having a paraffin wax coating thereon;

placing into said second receptacle a second support surface having a hydrophobic material coating thereon;

introducing into each of said first and second receptacles said body specimen;

determining said presence of said nonparaffinophilic hydrophobic microorganism in said body specimen by observing (i) lack of microorganism growth on said paraffin coated material of said first support surface, (ii) a presence of microorganism growth on said hydrophobic material coating of said second support surface; and further confirming said presence of said nonparaffinophilic hydrophobic microorganism in said body specimen by performing a DNA extraction procedure.

2. The method of claim 1, wherein said DNA extraction procedure comprises:

(i) removing at least a portion of said hydrophobic material coating including said microorganism growth;

(ii) separating crude nucleic acid fractions from said microorganism growth;

(iii) destroying proteins in said crude nucleic acid fractions to create a lysate; and (iv) introducing said lysate into an anionic column chromatograph in order to obtain a pure DNA fraction.

3. The method of claim 2, including employing said pure DNA fraction to identify said microorganism growth.

4. The method of claim 2, including employing said pure DNA fraction for DNA manipulation processes.

5. The method of claim 1, including separating said cellular wall material from said cellular content by adding liquid lysozyme to said removed layer of hydrophobic material containing said microorganism growth.

6. The method of claim 5, including destroying said proteins by employing Proteinase K.

7. The method of claim 1, including said hydrophobic nonparaffinophilic is selected from the group consisting of *M. tuberculosis complex, M. paratuberculosis, M. leprae*, pseudomonads, and nocardial species.

8. The method of claim 1, wherein said first receptacle is a test tube; and said first support surface is a glass slide.

9. The method of claim 8, wherein said second receptacle is a test tube; and said second support surface is a glass slide.

10. The method of claim 1, wherein said hydrophobic coating material is selected from the group consisting of waxes, silicones and plastics.

11. The method of claim 10, wherein said plastics include polypropylene, polyethylene, polystyrene and tetrafluoroethylene.

12. The method of claim 1, wherein said body specimen is sputum, fecal matter, cerebrospinal fluid, urine, gastric fluid, lymphatic material and purulent body fluids.

13. A method of obtaining pure DNA fractions from microorganism growth on a hydrophobic material, said method comprising:

(i) removing at least a portion of said hydrophobic material coating including said microorganism growth;

(ii) separating crude nucleic acid fractions from said microorganism growth;

(iii) destroying proteins in said crude nucleic acid fractions to create a lysate; and (iv) introducing said lysate into an anionic column chromatograph in order to obtain a pure DNA fraction.

14. The method of claim 13, including emloying said pure DNA fraction to identify said microorganism growth.

15. The method of claim 13, including employing said pure DNA fraction for DNA manipulation processes.

16. The method of claim 13, including separating said cellular wall material from said cellular content by adding liquid lysozyme to said removed layer of hydrophobic material containing said microorganism growth.

17. The method of claim 16, including destroying said proteins by employing Proteinase K.

* * * * *